US011564750B2

United States Patent
Lalys et al.

(10) Patent No.: US 11,564,750 B2
(45) Date of Patent: Jan. 31, 2023

(54) METHOD AND SYSTEM FOR ASSISTANCE IN GUIDING AN ENDOVASCULAR INSTRUMENT

(71) Applicant: THERENVA, Rennes (FR)

(72) Inventors: Florent Lalys, Rennes (FR); Mathieu Colleaux, Rennes (FR); Vincent Durrmann, Rennes (FR); Antoine Lucas, Rennes (FR); Cemil Goksu, Rennes (FR)

(73) Assignee: THERENVA, Rennes (FR)

( * ) Notice: Subject to any disclaimer, the term of this patent is extended or adjusted under 35 U.S.C. 154(b) by 243 days.

(21) Appl. No.: 16/619,865

(22) PCT Filed: Jun. 5, 2018

(86) PCT No.: PCT/EP2018/064744
§ 371 (c)(1),
(2) Date: Dec. 5, 2019

(87) PCT Pub. No.: WO2018/224485
PCT Pub. Date: Dec. 13, 2018

(65) Prior Publication Data
US 2020/0178916 A1 Jun. 11, 2020

(30) Foreign Application Priority Data
Jun. 6, 2017 (FR) ...................................... 1755011

(51) Int. Cl.
*A61B 34/20* (2016.01)
*A61B 6/00* (2006.01)
(Continued)

(52) U.S. Cl.
CPC .............. *A61B 34/20* (2016.02); *A61B 6/481* (2013.01); *A61B 6/487* (2013.01); *A61B 6/504* (2013.01);
(Continued)

(58) Field of Classification Search
CPC .. A61B 6/00; A61B 6/032; A61B 6/48; A61B 6/481; A61B 6/486; A61B 6/487;
(Continued)

(56) References Cited

U.S. PATENT DOCUMENTS 6,961,406 B2 * 11/2005 Hayashi ............... A61B 6/4225
378/98.12
8,873,708 B2 * 10/2014 Sugiyama .............. A61B 6/542
378/62
(Continued)

FOREIGN PATENT DOCUMENTS

FR 2884703 A1 10/2006
FR 2942124 A1 8/2010
(Continued)

OTHER PUBLICATIONS

International Search Report dated Jul. 17, 2018 for corresponding International Application No. PCT/EP2018/064744, filed Jun. 5, 2018.
(Continued)

*Primary Examiner* — Carolyn A Pehlke
(74) *Attorney, Agent, or Firm* — David D. Brush; Westman, Champlin & Koehler, P.A.

(57) ABSTRACT

A system for assisting guiding an endovascular instrument in vascular structures of an anatomical region of interest of a patient. This system includes an imaging device for capturing three-dimensional images of parts of the body of a patient, a programmable device and a viewing unit. The imaging device captures partially superposed fluoroscopic images of the region, and the programmable device forms a first augmented image, representative of a complete panorama of bones of the region, and cooperates with the imaging device to obtain a second augmented image including a representation of the vascular structures of the region. The imaging device captures a current fluoroscopic image of
(Continued)

a part of the region, and the programmable device registers the current fluoroscopic image with respect to the first augmented image and locates and displays, on the viewing unit, an image region corresponding to the current fluoroscopic image in the second augmented image.

14 Claims, 7 Drawing Sheets

(51) Int. Cl.
*G06T 7/30* (2017.01)
*A61B 90/00* (2016.01)
(52) U.S. Cl.
CPC .......... *A61B 6/5235* (2013.01); *A61B 6/5241* (2013.01); *A61B 6/463* (2013.01); *A61B 6/488* (2013.01); *A61B 2090/376* (2016.02); *G06T 7/30* (2017.01); *G06T 2200/32* (2013.01); *G06T 2207/10121* (2013.01)
(58) Field of Classification Search
CPC ..... A61B 6/504; A61B 6/5211; A61B 6/5241; G06T 7/0012; G06T 7/30; G06T 7/33; G06T 7/337; G06T 7/38; G06T 2200/32; G06T 2207/10121
See application file for complete search history.

(56) References Cited

U.S. PATENT DOCUMENTS

| | | | |
|---|---|---|---|
| 2007/0140427 A1* | 6/2007 | Jensen | A61B 6/481 378/98.12 |
| 2010/0208973 A1 | 8/2010 | Lienard et al. | |
| 2011/0235889 A1* | 9/2011 | Spahn | G06T 5/50 382/132 |
| 2012/0050327 A1* | 3/2012 | Takekoshi | A61B 6/5241 345/634 |
| 2018/0161099 A1 | 6/2018 | Dumenil et al. | |
| 2018/0214103 A1* | 8/2018 | Okubo | A61B 6/504 |
| 2018/0368793 A1* | 12/2018 | Goto | A61B 6/4452 |
| 2019/0320995 A1* | 10/2019 | Amiri | A61B 34/00 |

FOREIGN PATENT DOCUMENTS

| | | |
|---|---|---|
| FR | 3037785 A1 | 12/2016 |
| WO | 2006063141 A2 | 6/2006 |

OTHER PUBLICATIONS

English translation of the International Written Opinion dated Jul. 17, 2018 for corresponding International Application No. PCT/EP2018/064744, filed Jun. 5, 2018.

* cited by examiner

METHOD AND SYSTEM FOR ASSISTANCE IN GUIDING AN ENDOVASCULAR INSTRUMENT

CROSS-REFERENCE TO RELATED APPLICATIONS

This Application is a Section 371 National Stage Application of International Application No. PCT/EP2018/064744, filed Jun. 5, 2018, the content of which is incorporated herein by reference in its entirety, and published as WO 2018/224485 on Dec. 13, 2018, not in English.

FIELD OF THE DISCLOSURE

The present invention relates to a system for assistance in guiding an endovascular instrument in vascular structures of an anatomical region of interest of a patient, for example a lower limb of a patient. It also relates to a method and a device for assistance in guiding an endovascular instrument in associated vascular structures.

It has an application in the field of image-guided endovascular interventions.

BACKGROUND OF THE DISCLOSURE

Endovascular interventions make it possible to treat vascular diseases in a minimally invasive manner. It generally consists in inserting by endovascular technique a medical device with the purpose of interacting with the pathological tissues. Endovascular interventions are in particular used to treat stenosis and arterial thrombosis, via the introduction of various suitable endovascular instruments such as a balloon or a stent.

Contrary to conventional surgical interventions that require carrying out a large opening of the body of the patient in order to access the tissues of interest, endovascular interventions require only fine incisions in order to be able to insert the instruments into the vascular structure. They have several advantages, in particular an increase in the short term as well as a decrease in intraoperative morbidity and in the duration of hospitalisation. Despite the generalisation of these interventions, they remain delicate and must be secured and made reliable. Access to the pathological tissues is made difficult by the nature of the intervention. Manipulating and controlling endovascular instruments require substantial precision in order to favour the success of the treatment. Moreover, following operating gestures can be carried out only through the intermediary of intraoperative imaging.

In the field of endovascular interventions two-dimensional images captured via fluoroscopy are used, which make it possible to guide the insertion of medical devices, such as catheters, into the femoral artery and in other vascular branches.

Fluoroscopy designates a medical imaging technique that uses X-rays that makes it possible to view anatomical structures that are in motion and in real time, in particular bone structures.

As the arteries are soft tissue and therefore not visible with X-rays, a radio-opaque contrast agent is administered to the patient so as to opacify the vascular structure and view the paths of the arteries. Useable images can then be obtained. This technique of capturing images of the vascular structures, in particular the arteries, of a patient is known as angiography, and the images obtained are called angiographic images.

The two-dimensional fluoroscopic and angiographic images are captured and used during an operative phase, therefore an intervention phase.

In general, conventional operating rooms are provided with a device for supporting an X-ray imaging device, known as a hoop or a C-arm device, that is mobile, and that makes it possible to capture fluoroscopic and angiographic images with a given field of vision.

In the particular case of endovascular procedures for treating obliterative arteriopathy of the lower limbs, there is an interest in obtaining images of an entire lower limb of the patient. However as the field of vision of an image capturing device is limited, it is necessary to capture a plurality of fluoroscopic and angiographic images, preferably partially superposed, in order to obtain via image processing a composite or panoramic image of an anatomical region of interest, for example of a lower limb of the patient in its entirety.

In addition, in the framework of conventional endovascular interventions, for the treating of lower limbs, if the arterial occlusions are of large size or are obscured, they cannot be viewed on a single angiographic image, therefore several angiographic image captures are required, in a first step in order to view all of the lesions to be treated, then, in a second step, in order to precisely carry out the treatment of each lesion.

However, each angiographic image capture requires the injection of a contrast agent, which is toxic for the patient. For example, an iodinated contrast agent is nephrotoxic.

In addition, each additional image capture exposes the patient and the medical personnel present in the operating room to an additional quantity of X-rays.

SUMMARY

An exemplary embodiment of the present invention proposes a system for assistance in guiding an endovascular instrument in vascular structures of an anatomical region of interest of a patient, comprising an imaging device suitable for capturing two-dimensional images of parts of the body of a patient, a programmable device and a viewing unit, characterised in that:

- the imaging device is suitable for capturing a plurality of partially superposed fluoroscopic images of the anatomical region of interest, and the programmable device is configured to form a first augmented image representative of a complete panorama of the bones of said anatomical region of interest,
- the programmable device is configured to cooperate with the imaging device in order to obtain a second augmented image including a representation of the vascular structures of said anatomical region of interest,
- the imaging device is configured to capture a new fluoroscopic image, called the current fluoroscopic image, of a part of the anatomical region of interest,
- the programmable device is configured to register said current fluoroscopic image with respect to the first augmented image,
- to locate and display, on the viewing unit an image region corresponding to the current fluoroscopic image in the second augmented image.

Advantageously, the system of an exemplary embodiment of the invention comprises the displaying of an image region corresponding to a current fluoroscopic image in an augmented image including a representation of the vascular structures of the portion of the anatomical region of interest that can be viewed in the current fluoroscopic image, without the need to re-inject radio-opaque contrast agent into the body of the patient.

The system according to an exemplary embodiment of the invention can also have one or several of the characteristics hereinbelow, taken individually or according to any technically permissible combinations.

The programmable device is configured to display markers that delimit arterial lesions observed on the second augmented image.

The second augmented image is a two-dimensional image representative of an arterial panorama of the anatomical region of interest, the programmable device being configured to control the imaging device in order to capture a plurality of angiographic images corresponding to the plurality of fluoroscopic images.

The programmable device is configured to control the imaging device in order to capture a plurality of angiographic images substantially in parallel with the capturing of a plurality of partially superposed fluoroscopic images, the imaging device being at the same spatial position for the capturing of a fluoroscopic image and of a corresponding angiographic image.

The programmable device is configured to carry out a merger of the first augmented image and of the second augmented image and a displaying on the viewing unit of the merged image.

The programmable device is configured to in addition display on the viewing unit an image region corresponding to the current fluoroscopic image in the merged image.

The programmable device is configured to, in a pre-operative phase, cooperate with the imaging device in order to obtain a third augmented image representative of the bone and vascular structures of the anatomical region of interest, and, after locating an image region corresponding to the current fluoroscopic image in the second augmented image, locating and displaying an image region corresponding to the current fluoroscopic image in the third augmented image.

The second augmented image is a three-dimensional image representative of the bone and vascular structures of the anatomical region of interest, and wherein the programmable device is configured to, during the cooperation with the imaging device in order to obtain a second augmented image, obtain and memorise, in a pre-operative phase, said three-dimensional image.

According to another aspect, an exemplary embodiment of the invention relates to a method for guiding an endovascular tool in vascular structures of an anatomical region of interest of the patient. This method comprises the steps of:
  capturing a plurality of partially superposed two-dimensional fluoroscopic images of the anatomical region of interest of the patient, and forming a first augmented image representative of a complete panorama of the bones of said anatomical region of interest,
  obtaining a second augmented image including a representation of the vascular structures of said anatomical region of interest,
  capturing a new two-dimensional fluoroscopic image, called the current fluoroscopic image, of a portion of said anatomical region of interest,
  registering the current fluoroscopic image with respect to the first augmented image,
  locating and displaying an image region corresponding to the current fluoroscopic image in the second augmented image.

The method according to an exemplary embodiment of the invention can also have one or several of the characteristics hereinbelow, taken individually or according to any technically permissible combinations.

The method further comprises a step of displaying markers that delimit arterial lesions observed on the second augmented image.

The second augmented image is a two-dimensional image representative of an arterial panorama of the anatomical region of interest, with the step of obtaining a second augmented image comprising the capturing of a plurality of angiographic images corresponding to the plurality of fluoroscopic images.

The capturing of a plurality of angiographic images is carried out substantially in parallel with the capturing of a plurality of partially superposed fluoroscopic images, at the same spatial position for the capturing of a fluoroscopic image and of a corresponding angiographic image.

The method comprises a merger of the first augmented image and of the second augmented image and a displaying of the merged image.

It further comprises a displaying of an image region corresponding to the current fluoroscopic image in the merged image.

It further comprises, in a pre-operative phase, the obtaining of a third augmented image representative of the bone and vascular structures of the anatomical region of interest, and, after the step of locating an image region corresponding to the current fluoroscopic image in the second augmented image, a step of locating and of displaying another image region corresponding to the current fluoroscopic image in the third augmented image.

The second augmented image is a three-dimensional image representative of the bone and vascular structures of the anatomical region of interest, and the step of obtaining a second augmented image comprises the obtaining and the memorising, in a pre-operative phase, of said three-dimensional image.

According to another aspect, an exemplary embodiment of the invention relates to a computer program that includes instructions for implementing the steps of a method for assistance in guiding an endovascular instrument in vascular structures such as described briefly hereinabove, during the execution of the program by a processor of a programmable device.

According to another aspect, an exemplary embodiment of the invention relates to a programmable device for assistance in guiding an endovascular instrument in vascular structures of an anatomical region of interest of a patient, suitable for cooperating with an imaging device suitable for capturing two-dimensional images of parts of the body of a patient, and with a viewing unit. This device is suitable for:
  obtaining a plurality of partially superposed fluoroscopic images of the anatomical region of interest, and forming a first augmented image representative of a complete panorama of the bones of said anatomical region of interest,
  obtaining a second augmented image including a representation of the vascular structures of said anatomical region of interest,
  obtaining a new fluoroscopic image, called the current fluoroscopic image, of a part of the anatomical region of interest,
  registering said current fluoroscopic image with respect to the first augmented image, to locate and display, on the viewing unit an image region corresponding to the current fluoroscopic image in the second augmented image.

BRIEF DESCRIPTION OF THE DRAWINGS

Other characteristics and advantages shall appear in the description that is given of it hereinbelow, for the purposes of information and in a non-limiting manner, in reference to the accompanying figures, among which.

DETAILED DESCRIPTION OF ILLUSTRATIVE EMBODIMENTS

The invention is described hereinafter more particularly for assistance in guiding an endovascular instrument in the lower limbs, but the invention more generally applies to other anatomical regions of interest, or to a wider region that also includes all or a portion of the trunk of the patient.

Figure 1:
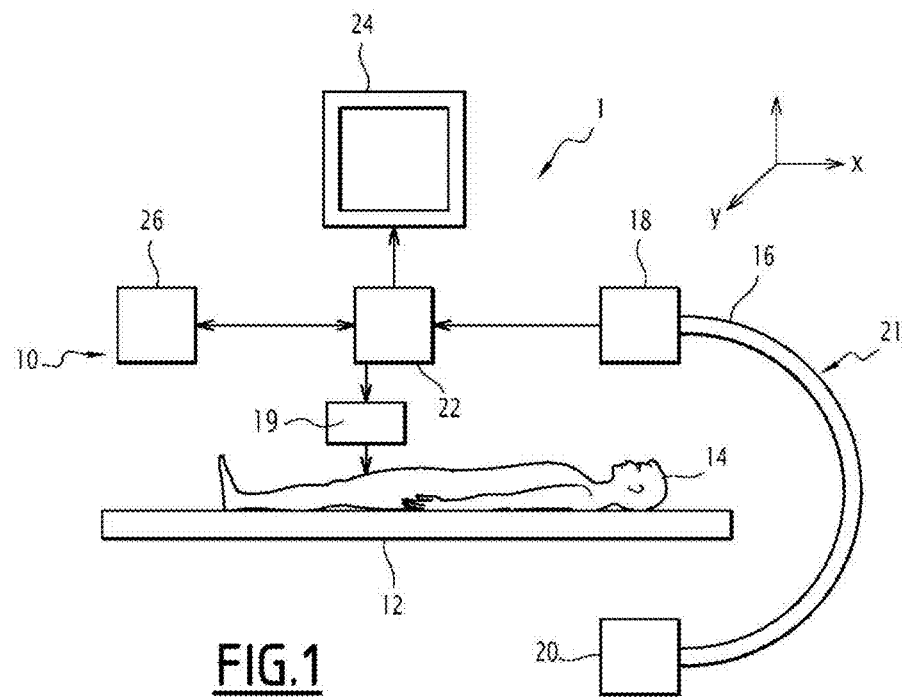
FIG. 1 diagrammatically shows an endovascular intervention system guided by the image.

FIG. 1 diagrammatically shows an operating room 1, provided with an image-guided endovascular intervention system 10.

The operating room 1 is provided with an operating table 12, whereon is represented a patient 14 to be treated via an endovascular intervention.

The intervention system 10 comprises an X-ray imaging device 21, itself comprised of a support device 16 in the shape of a hoop, of a source 18 of X-rays and of a unit 20 for receiving and detecting X-rays, positioned facing the source 18. This imaging device is suitable for capturing images of elements positioned between the source 18 of X-rays and the unit 20 for receiving and detecting, and is also suitable for rotating about two axes according to the needs of the operator.

The two-dimensional images captured by an X-ray imaging system are generally called fluoroscopic images.

Thus, the imaging device 21 shows is suitable for capturing fluoroscopic two-dimensional images of various anatomical regions of interest of the body of the patient, comprising targeted vascular structures, in particular the arteries.

In particular, the operator can displace the imaging device 21 substantially in translation along the legs of the patient 14, in order to capture a plurality of N fluoroscopic images $F_i$.

More generally, the operator can displace the imaging device 21 substantially in translation in order to obtain a plurality of fluoroscopic images of an anatomical region of interest chosen or extending from the supra-aortic trunk to the feet of the patient.

Alternatively, the displacement in translation of the imaging device 21 is controlled, for example by the programmable device 22, described hereinafter.

The number N of images to be captured is chosen according to the field of vision of the imaging device and the size of the patient 14. For example, 3 to 4 images of each leg of the patient 14 are captured along the axis of the femur.

The imaging device is positioned at successive positions such that two images captured successively have a partial superposition on a rectangular superposition region, of a predetermined or variable size.

Preferably, the superposition region has a surface greater than or equal to 20% of the surface of the two-dimensional images captured.

The imaging device 21 is also suitable for capturing angiographic images $A_i$ of the leg or of the legs of the patient, following an injection of a radio-opaque contrast agent by an injection unit 19.

As shall be explained in more detail in what follows, in an embodiment of the invention, during a first preparatory operative phase, at each successive position of the imaging device, a corresponding fluoroscopic image and angiographic image are captured and memorised in the form of two-dimensional digital images.

The intervention system 10 also comprises a programmable device 22, comprising one or several processors, associated with a viewing unit 24 comprised of one or several screens and of a man-machine interface 26.

The man-machine interface 26 comprises means for pointing and selecting elements, for example a keyboard-mouse unit, a touchpad, a contactless 3D gesture interface or a combination of these devices.

In an embodiment, the man-machine interface 26 is integrated with the viewing unit 24 in the form of a touch screen.

The programmable device 22 is suitable for receiving the two-dimensional images (fluoroscopic and/or angiographic) captured by the X-ray imaging device and for processing them according to a method for assistance in guiding an endovascular instrument in vascular structures according to an exemplary embodiment of the invention.

In an embodiment, the programmable device 22 is suitable for controlling the capturing of two-dimensional images (fluoroscopic and/or angiographic).

The two-dimensional images captured during the intervention phase are displayed on the viewing unit 24 in order to assist in the precise guiding of the endovascular instruments inside the vascular structures, in particular the arteries, of the patient.

The endovascular instruments are selected from among a catheter, an endovascular device of the stent type, a flexible or rigid guide, an endoprosthesis or a balloon.

Figure 2:
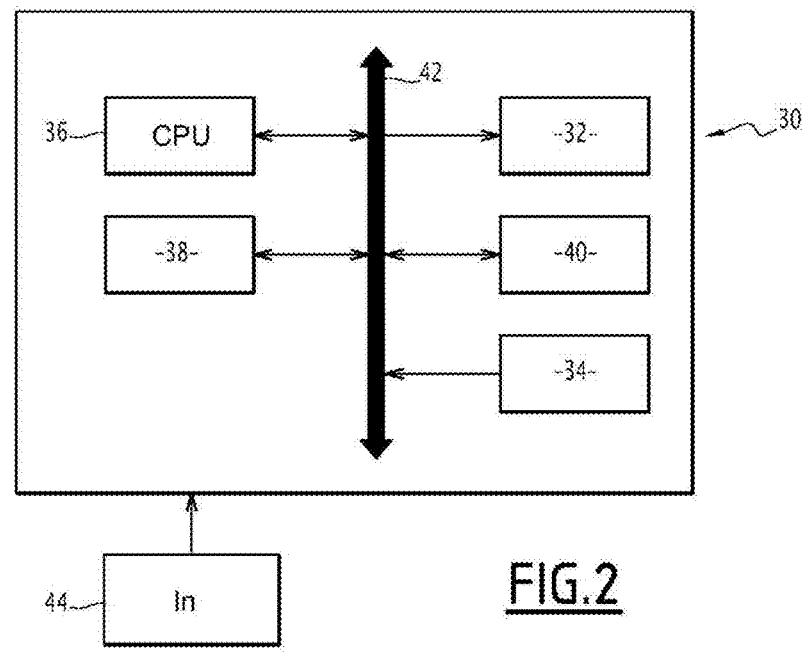
FIG. 2 is a block diagram of the main blocks of a programmable device suitable for implementing the method of an exemplary embodiment of the invention.

FIG. 2 shows the main blocks of a programmable device 30 suitable for implementing the method for assistance in guiding an endovascular instrument in vascular structures according to an embodiment of the invention.

A programmable device 30 able to implement the invention, comprises a screen 32, similar to the viewing unit 24, a unit 34 for the entering of the commands of an operator, for example a keyboard, a mouse, a touchpad or a contactless interface, similar to the unit 26, a central processing unit 36, or CPU, able to execute computer program instructions when the device 30 is turned on. The device 30 optionally comprises a controller 40, that makes it possible to send commands and to select elements remotely.

The device 30 also comprises a data storage unit 38, for example registers, suitable for storing executable code instructions that allow for the implementing of programs that comprise code instructions able to implement the method according to an exemplary embodiment of the invention. The various functional blocks of the device 30 described hereinabove are connected via a communication bus 42.

The device 30 is able to receive image data from a source 44.

In an embodiment, the device 30 is suitable for cooperating with an imaging device in order to capture fluoroscopic and/or angiographic images. In particular, the device 30 is suitable for commander the imaging device in order to capture a plurality of angiographic images corresponding to the plurality of fluoroscopic images.

The method of an exemplary embodiment of the invention is suitable for being implemented by a programmable device 30 such as a computer integrated into a standard operating room, which makes it possible to limit equipment costs.

In an embodiment, the method of the invention is implemented by software code modules. The executable code instructions are recorded on a support that can be read by a computer, for example an optical disc, a magnetic-optical disc, a ROM memory, a RAM memory, a non-volatile memory (EPROM, EEPROM, FLASH, NVRAM), a magnetic or optical card. Alternatively the software code modules are carried out in the form of a programmable logic component such as a FPGA (for Field Programmable Gate Array), or in the form of a dedicated integrated circuit such as an ASIC (for Application Specific Integrated Circuit).

The programmable device 30 is suitable for:
- obtaining a plurality of partially superposed fluoroscopic images of the anatomical region of interest, and forming a first augmented image representative of a complete panorama of the bones of said anatomical region of interest,
- obtaining a second augmented image including a representation of the vascular structures of said anatomical region of interest,
- obtaining a new fluoroscopic image, called the current fluoroscopic image, of a part of the anatomical region of interest,
- registering said current fluoroscopic image with respect to the first augmented image, to locate and display, on the viewing unit an image region corresponding to the current fluoroscopic image in the second augmented image.

Figure 3:
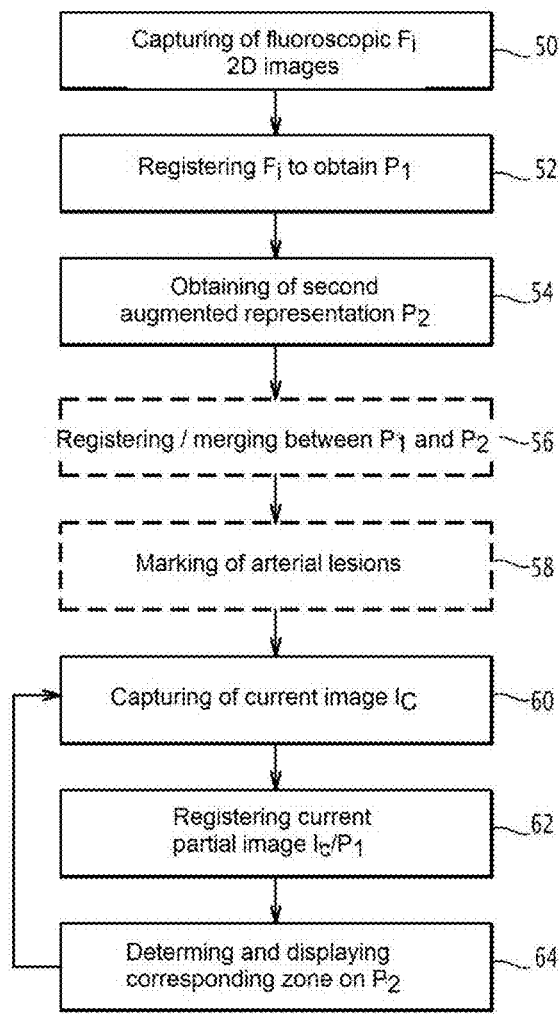
FIG. 3 is a flowchart of the main steps of a method for assistance in guiding an endovascular instrument according to an exemplary embodiment of the invention.

FIG. 3 shows the main steps implemented in a method for assistance in guiding an endovascular instrument in vascular structures according to an embodiment of the invention, implemented by a processor 36.

The method comprises, in a first operative phase, a first step 50 of capturing N two-dimensional fluoroscopic images of a lower limb of the patient, for example 3 or 4 successive images captured by translation of the imaging device along the axis of the femur.

The two-dimensional fluoroscopic images are noted as $\{F_1, \ldots F_i, \ldots F_N\}$ and are memorised in the form of digital images. Two successive images are partially superposed, and therefore have a rectangular superposition region of variable size when the device is displaced by the operator, preferably greater than or equal to a predetermined size.

For example, when each digital image is represented in the form of a two-dimensional matrix of pixels, with each pixel having an associated numerical value called intensity, the size of the image is defined by a number of lines and number of columns, a superposition region comprises a number of lines and of columns that form a region of a given surface, preferably greater than or equal to 20% of the entire surface of the image.

The step 50 is followed by a step 52 of two-by-two registering of the two-dimensional fluoroscopic images for forming a first augmented image, noted as $P_1$, representative of a complete panorama of the bones of the lower limb represented.

The registering of images, or setting in spatial correspondence, consists in placing in spatial correspondence anatomical or functional structures present in each one of the images. Via the successive merging of registered images along the lower limb, an augmented image is obtained that represents the bone structure of the entire lower limb.

In the present case of application, the purpose of the registering is to carry out a precise superposition of the bone structures present in the superposition region that is common to the successive images.

Two successive images can have a slight rotation between them, in particular when the operator displaces the imaging device. The registering 2D/2D consists in optimising two translations and one rotation.

The two-dimensional fluoroscopic images captured have a level of contrast that is relatively substantial thanks to the bones. There are several methods of rigid registering between two-dimensional images (or 2D/2D registering) that can be applied for images that include objects that have a relatively high level of contrast.

For example, an automatic registering of the iconic type can be implemented, by using a measurement of similarity based on the difference of gradients between the two images, coupled to an optimisation strategy of the gradient descent type or Powell optimiser.

Following the step 52 of 2D-2D registering a first augmented image $P_1$ is obtained that represents a panorama of the bones of the lower limb of the patient. As explained hereinabove the image $P_1$ is obtained from a plurality of captured fluoroscopic two-dimensional images.

During a step 54, at least one second augmented image of the lower limb of the patient is obtained. This second augmented image comprises a representation of the vascular structures of the lower limb of the patient.

Two embodiments different from the step 54 are considered and shall be described in more detail hereinafter in reference to FIGS. 4 and 5.

In a first embodiment, the second augmented image is a two-dimensional image representative of an arterial panorama of the lower limb considered, located in the same spatial reference system as the panorama of the bones $P_1$.

The arterial panorama is obtained from two-dimensional angiographic images representing the vascular structures of the lower limb considered. As the angiographic images obtained are in the same spatial reference system as the fluoroscopic images, the registering parameters obtained in the step 50 are directly applied to the angiographic images in order to obtain the arterial panorama.

In a second embodiment, the second augmented image is a three-dimensional image of the bone and vascular structures of the lower limb considered. In this second embodiment, the second augmented image is obtained in a prior, pre-operative and memorised phase. It is for example calculated from images obtained by capturing techniques such as for example tomography also called CT for "computed tomography", magnetic resonance imaging (MRI), enhanced by the injection of a contrast agent in order to have the vascular structures appear better.

In a third embodiment, a second augmented image representative of an arterial panorama and a third three-dimensional image of the bone and vascular structures of the lower limb considered are both used.

In the case of obtaining an augmented image of the pre-operative three-dimensional image, the step 54 is followed by an optional step 56 of registering between the first and second augmented images.

Following the step 56, it is useful to represent a merged image $P_3$ of the panorama of the bones $P_1$ and of the augmented image $P_2$, which will be used for the simultaneous viewing of bone and arterial structures.

The step 56 or the step 54 is optionally followed by a step 58 of marking, by the operator of the system, for example a doctor, the arterial lesions observed on the second augmented image $P_2$.

In a second operative phase, a current fluoroscopic image $I_c$ is captured in the step 60. The second operative phase is an effective intervention phase, during which an endovascular instrument, selected from among a catheter, an endovascular device of the stent type, a flexible or rigid guide, an endoprothesis or a balloon, is inserted in order to treat the patient.

The current fluoroscopic image $I_c$ is then registered with respect to the first augmented image $P_1$ representative of a panorama of the bones of the lower limb in the step 62.

Registering consists here in placing in spatial correspondence of the bone anatomical structures present in the current fluoroscopic image $I_c$ with structures of the first augmented image $P_1$. The registering used here is thus of the "template matching" type due to the belonging of the current image $I_c$ to a very precise portion of the first augmented image $P_1$.

Preferably, the registering carried out is of the iconic type, by using a measurement of the similarity based on the difference in gradients between the two images, a measurement of similarity based on mutual information, or a combination of the two.

Finally, in the step 64, an image region corresponding to the current fluoroscopic image $I_c$ is determined in the second augmented image $P_2$ and/or in the merged image $P_3$, and is displayed, thanks to the calculated and memorised registering information between the first augmented image $P_1$ and the second augmented image $P_2$.

Advantageously, the local vascular structure is displayed in liaison with the current fluoroscopic image without requiring a new capturing of an angiographic image, and consequently without requiring injecting a supplement of contrast agent.

Advantageously, in the case where the marking of the lesions was carried out during the step 58, the lesions are located precisely in relation to the current fluoroscopic image thanks to the registering carried out between the current fluoroscopic image and the first augmented image $P_1$ and thanks to the registering between the first augmented image $P_1$ and the second augmented image $P_2$.

The steps 60 to 64 are reiterated substantially in real time as many times as needed during the intervention, in particular for each lesion to be treated on the lower limb.

Figure 4:
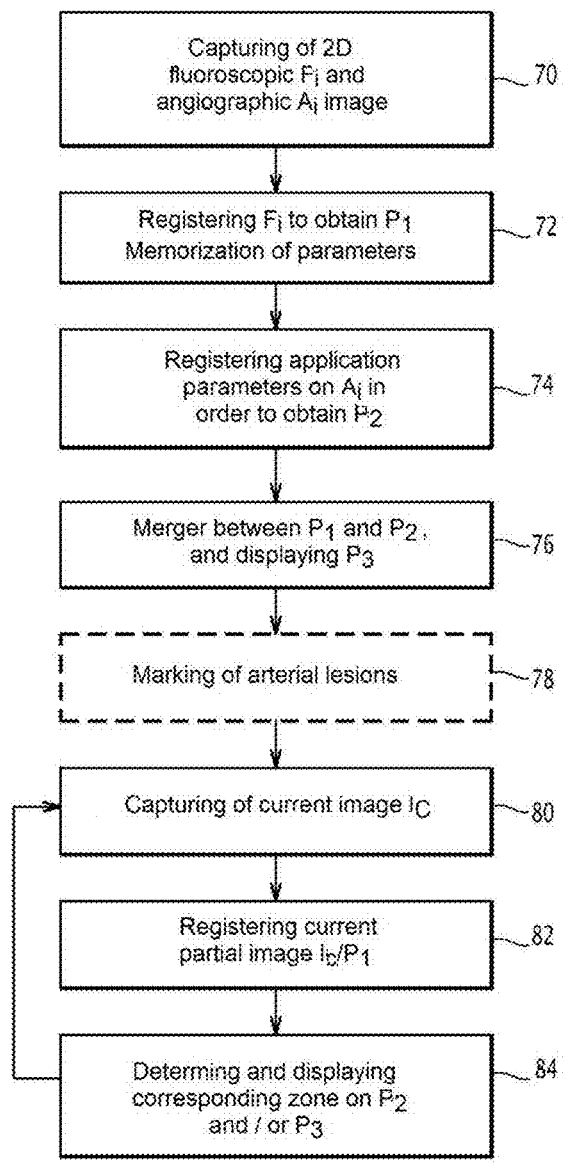
FIG. 4 is a flowchart of the main steps of a method according to a first embodiment.

FIG. 4 shows in more detail a first embodiment of the invention, wherein the second augmented image $P_2$ is an arterial panorama of the lower limb of the patient.

In this first embodiment, in the step of capturing images 70, at each image capturing position of the imaging device, a fluoroscopic image $F_i$ and an angiographic image $A_i$ are captured. Thus, there is an initial spatial correspondence between these images. In other terms, the images are captured in the same spatial reference system.

The step 72 of registering is similar to the step 52 described hereinabove. The rigid 2D-2D registering parameters between successive fluoroscopic images are memorised, and then applied in the step 74 to the angiographic images $A_i$ in order to obtain the second augmented image $P_2$.

Thus, advantageously, the registering parameters are calculated on the fluoroscopic images that have a good contrast thanks to the presence of the bone structures. Thanks to the capturing of fluoroscopic and angiographic images in spatial correspondence, a panorama of vascular structures that corresponds to the panorama of bones is easily obtained.

The first and second augmented images are merged in the step of fusion 76 in a merged image $P_3$ that shows both the bone and vascular structures of the entire lower limb studied. The merger includes for example a sum that is weighted by weighting coefficients, pixel by pixel, of the augmented images $P_1$ and $P_2$, with the weighting coefficients associated with the respective pixels being chosen according to the initial intensity of the images.

The image $P_3$ is displayed, for example next to the second augmented image $P_2$. Of course, alternative displays can be considered.

In the optional step of marking 78, the operator adds markers, of which the position is recorded, in order to mark the arterial lesions to be treated.

The markers are more preferably added on the second augmented image $P_2$ representative of the panorama of the vascular structures, and added precisely on the merged image $P_3$. The markers are for example represented by coloured lines superposed on the image or images displayed.

Alternatively, the markers are added on the second augmented image $P_2$ before the step 76 of calculating the merged image $P_3$, and are added on the merged image displayed.

According to another alternative, the markers are added directly on the merged image $P_3$.

The step 80 of capturing a current fluoroscopic image $I_c$ is similar to the step 60 described hereinabove.

The current fluoroscopic image is then registered with respect to the first augmented image $P_1$ in the step 82, similar to the step 62 described hereinabove.

Then, in the step 84, the vascular structures corresponding to the current fluoroscopic image are relocated in the second augmented image $P_2$ and/or in the merged image $P_3$, and are displayed.

Figure 6:
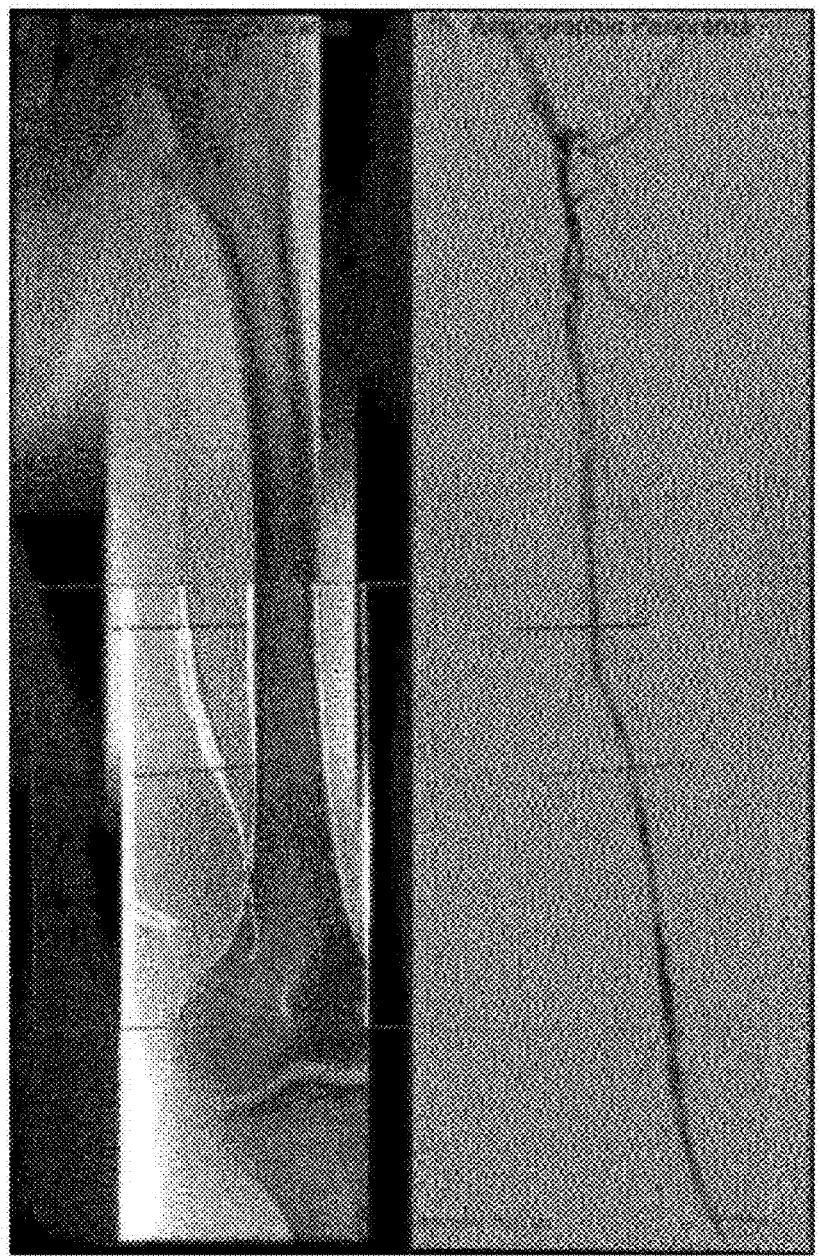
FIG. 6 is an example of the display of the first and second augmented images according to an embodiment.

For example, in an embodiment, a frame indicating the region that corresponds to the current fluoroscopic image is displayed, both on the augmented image $P_2$ and the merged image $P_3$, which are displayed in parallel, as well as the previously positioned marked, as shown in the example of FIG. 6.

In FIG. 6, the left portion shows a merged image, comprising the panorama of bones of the first augmented image merged with the current fluoroscopic image, as well as markers for delimiting an arterial lesion. In parallel, on the right portion of the figure, the second augmented image representative of the arterial panorama is represented, also with markers for delimiting the same arterial lesion.

Figure 7:
FIG. 7 is an example of the display as superposition of fluoroscopic and angiographic data.

In addition, according to an alternative, an image representative of the current fluoroscopic image with in superposition the corresponding angiographic structure, and, where applicable, with the previously recorded markers, is displayed, with a better display resolution than the resolution of the region displayed on the augmented image $P_2$ or on the image $P_3$ FIG. 7 shows an example of displaying a current fluoroscopic image, with as superposition the corresponding angiographic structure coming from the second augmented image.

Thus, advantageously, the arterial lesions to be treated are relocated, in liaison with the current fluoroscopic image and with the augmented $P_2$ and merged $P_3$ images of the lower limb, which makes it possible to assist in the guiding of the endovascular instrument during the intervention without a new capturing of an angiographic image.

Figure 5:
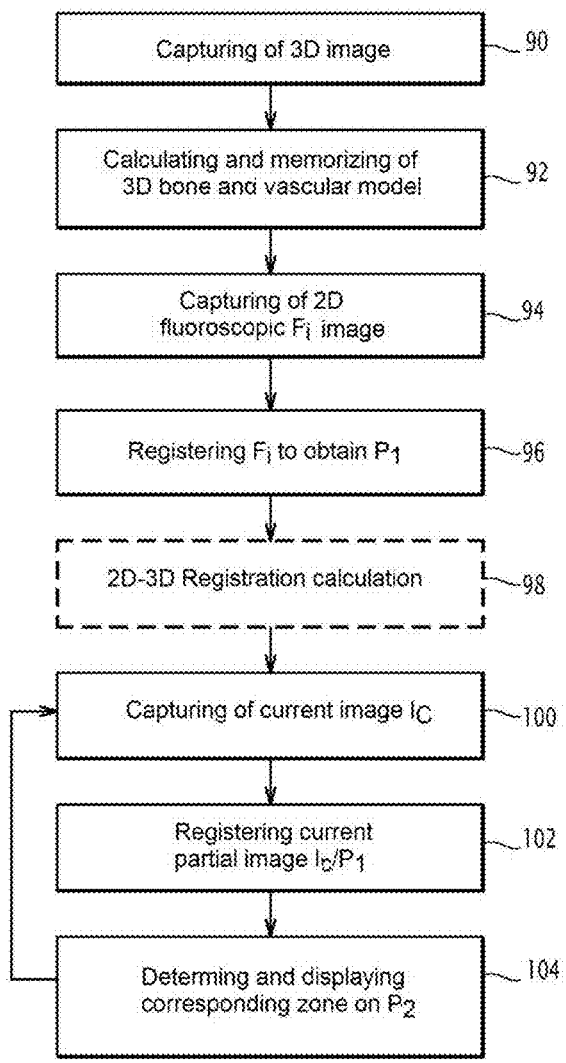
FIG. 5 is a flowchart of the main steps of a method according to a second embodiment.

FIG. 5 shows in more detail a second embodiment of the invention, wherein the second augmented image $P_2$ is a 3D image representative of the bone and vascular structures of the lower limb of the patient.

In this embodiment, the second augmented image $P_2$ is obtained and memorised in a pre-operative phase. This three-dimensional image is for example calculated from images obtained in the pre-operative step 90 by capturing techniques such as for example tomography also called CT for "computed tomography", magnetic resonance imaging (MRI), enhanced by the injection of a contrast agent in order to have the vascular structures appear better.

From the images obtained, a 3D image is calculated and memorised in the pre-operative step 92. There are various known methods for calculating such an image. For example, by working on the CT image obtained with the injection of a contrast agent, an automatic segmentation of the arterial structures can be used to create a three-dimensional anatomical model of the patient. A semi-automatic segmentation algorithm of the graph section type can be used.

For example, such a virtual three-dimensional anatomical model can include the segmented volumes of the femoral artery, internal iliac arteries, hips and the femur.

In operative phase, the method comprises a step 94 of capturing fluoroscopic two-dimensional images, similar to the step 50 described hereinabove, followed by a step of registering 96 in order to form the first augmented image $P_1$, similar to the step 52 described hereinabove.

A rigid 2D-3D registering is then applied in the step 98, and parameters that allow for the putting into correspondence of the first augmented image $P_1$ and the second augmented three-dimensional image are memorised.

Any known method of rigid 2D-3D registering can be applied. For example, a semi-automatic registering of the iconic type is implemented, wherein the initialisation of a portion of the points used for the registering is carried out manually, which makes it possible to have the two images to be registered correspond roughly, and automatic registering is then launched afterwards in order to refine the result.

The step 98 is followed by steps of capturing 100 a current fluoroscopic two-dimensional image, representative of a portion of the lower limb considered, similar to the step 60 described hereinabove, then a step 102 of registering with respect to the first augmented image $P_1$, similar to the step 62 already described.

Finally, during the step 104, a region corresponding to the current image is determined in the three-dimensional image $P_2$, by applying the parameters for putting into 2D-3D correspondence between the first augmented image $P_1$ and the three-dimensional image $P_2$ calculated and memorised in the step 98.

Alternatively, a 2D-3D registering is carried out in the step 104.

Finally, a region corresponding to the current fluoroscopic image is displayed on the three-dimensional image $P_2$.

Figure 8:
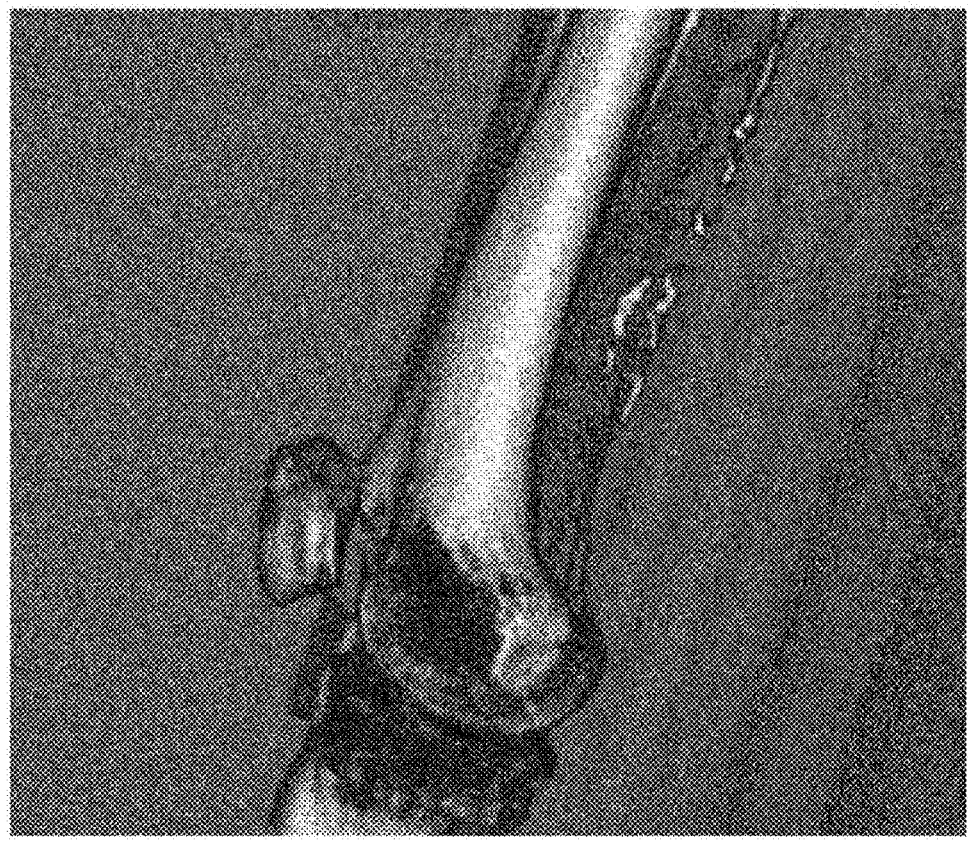
FIG. 8 is an example of a 3D representation of the bone and vascular structures.

FIG. 8 shows an example of a 3D image representative of the bone and vascular structures of a portion of a lower limb, superposed with a current fluoroscopic image.

Of course, alternatives in the detail of the implementing of the steps hereinabove, within the scope of those skilled in the art, can be entirely considered.

In a third embodiment, the first two embodiments are combined. The second augmented image $P_2$ representative of an arterial panorama is calculated and displayed, as in the first embodiment. In addition, another augmented image $P'_2$, which is the three-dimensional image representative of the bone and vascular structures of the lower limb, is also calculated and displayed as in the second embodiment.

The region corresponding to the current fluoroscopic image is determined and displayed on each one of the augmented images.

Thus, the method allows for the displaying, in the second operative phase, of a region corresponding to the current fluoroscopic image both in the augmented image corresponding to the arterial panorama, and in the three-dimensional augmented image.

Advantageously, the operator has information on the arterial lesions, as well as additional information on the patient, for example the location of the calcifications that are visible only in the 3D image.

In all of the embodiments, it is not necessary to inject the contrast agent and to capture new angiographic images that correspond to the current fluoroscopic images, therefore the quantity of contrast agent to be injected into the patient is decreased in relation to conventional interventions.

In addition, advantageously, more information is displayed, which makes it possible to improve the assistance provided in the framework of endovascular interventions.

An exemplary embodiment of the present invention therefore has an object to overcome the disadvantages of the known methods, in order to improve image-guided endovascular interventions while still limiting the number of angiographic image captures.

Although the present disclosure has been described with reference to one or more examples, workers skilled in the art will recognize that changes may be made in form and detail without departing from the scope of the disclosure and/or the appended claims.

The invention claimed is:

1. An apparatus comprising:
   a programmable device for assistance in guiding an endovascular instrument in vascular structures of an anatomical region of interest of a patient, the programmable device comprising:
   a processor; and
   a non-transitory computer-readable medium comprising instructions stored thereon, which when executed by the processor configure the programmable device to perform acts comprising:
   obtaining a plurality of partially superposed fluoroscopic images of the anatomical region of interest from an imaging device positioned at different successive positions that is configured to capture two-dimensional images of parts of the body of the patient, and forming a first augmented image representative of a complete panorama of bones of said anatomical region of interest,
   capturing a plurality of angiographic images corresponding to the plurality of fluoroscopic images, and forming a second augmented image, the second augmented image being a two-dimensional image representative of an arterial panorama of the anatomical region of interest, obtaining a new fluoroscopic image, called a current fluoroscopic image, of a part of the anatomical region of interest, and performing a template matching type registering of said current fluoroscopic image with respect to the first augmented image, so as to locate, based on a spatial correspondence of bone anatomical structures, a portion of the first augmented image corresponding to the current fluoroscopic image, and locating and displaying on a viewing unit an image region corresponding to said portion of the first augmented image in the second augmented image.

2. The apparatus according to claim 1, wherein the apparatus further comprises:
the viewing unit; and
the imaging device.

3. The apparatus according to claim 1, wherein the programmable device is configured to display markers that delimit arterial lesions observed on the second augmented image.

4. The apparatus according to claim 1, wherein the programmable device is configured to control the imaging device in order to capture the plurality of angiographic images substantially in parallel with the capturing of the plurality of partially superposed fluoroscopic images, the imaging device being at a same spatial position for the capturing of a fluoroscopic image and of a corresponding angiographic image.

5. The apparatus according to claim 1, wherein the programmable device is configured to carry out a merger of the first augmented image and of the second augmented image to create a merged image and display on the viewing unit the merged image.

6. The apparatus according to claim 5, wherein the programmable device is configured to display on the viewing unit an image region corresponding to the current fluoroscopic image in the merged image.

7. The apparatus according to claim 6 wherein the programmable device is configured to, in a pre-operative phase, cooperate with the imaging device in order to obtain a third augmented image representative of the bone and vascular structures of the anatomical region of interest, and, after locating an image region corresponding to the current fluoroscopic image in the second augmented image, locating and displaying an image region corresponding to the current fluoroscopic image in the third augmented image.

8. A non-transitory computer-readable medium comprising a computer program stored thereon comprising instructions for implementing a method for assistance in guiding an endovascular instrument in vascular structures during execution of the program by a processor of a programmable device, wherein the instructions configure the programmable device to:

capture with an imaging device positioned at different successive positions a plurality of partially superposed two-dimensional fluoroscopic images of an anatomical region of interest of the patient, and forming a first augmented image representative of a complete panorama of bones of said anatomical region of interest, capture a plurality of angiographic images corresponding to the plurality of fluoroscopic images, and forming a second augmented image, the second augmented image being a two-dimensional image representative of an arterial panorama of the anatomical region of interest, capture a new two-dimensional fluoroscopic image, called a current fluoroscopic image, of a portion of said anatomical region of interest, perform a template matching type registering of the current fluoroscopic image with respect to the first augmented image, so as to locate, based on a spatial correspondence of bone anatomical structures, a portion of the first augmented image corresponding to the current fluoroscopic image, and locate and display on a viewing unit an image region corresponding to said portion of the first augmented image in the second augmented image.

9. The non-transitory computer-readable medium according to claim 8, wherein the instructions further configure the programmable device to display markers that delimit arterial lesions observed on the second augmented image.

10. A method for assistance in guiding an endovascular instrument in vascular structures of an anatomical region of interest of the patient, the method comprising the following acts:

capturing with an imaging device positioned at different successive positions a plurality of partially superposed two-dimensional fluoroscopic images of the anatomical region of interest of the patient, and forming a first augmented image representative of a complete panorama of bones of said anatomical region of interest, capturing a plurality of angiographic images corresponding to the plurality of fluoroscopic images, and forming a second augmented image, the second augmented image being a two-dimensional image representative of an arterial panorama of the anatomical region of interest, capturing with the imaging device a new two-dimensional fluoroscopic image, called a current fluoroscopic image, of a portion of said anatomical region of interest, performing a template matching type registering of the current fluoroscopic image with respect to the first augmented image, so as to locate, based on a spatial correspondence of bone anatomical structures, a portion of the first augmented image corresponding to the current fluoroscopic image, and locating and displaying on a viewing unit an image region corresponding to said portion of the first augmented image in the second augmented image.

11. The method according to claim 10, further comprising displaying markers that delimit arterial lesions observed on the second augmented image.

12. The method according to claim 10, wherein the capturing of a plurality of angiographic images is carried out substantially in parallel with the capturing of a plurality of partially superposed fluoroscopic images, at a same spatial position for the capturing of a fluoroscopic image and of a corresponding angiographic image.

13. The method according to claim 10, comprising merging the first augmented image and of the second augmented image to create a merged image, displaying the merged image, and displaying an image region corresponding to the current fluoroscopic image in the merged image.

14. The method according to claim 13 further comprising, in a pre-operative phase, obtaining a third augmented image representative of the bone and vascular structures of the anatomical region of interest, and, after the locating an image region corresponding to the current fluoroscopic image in the second augmented image, locating and displaying another image region corresponding to the current fluoroscopic image in the third augmented image.

* * * * *